United States Patent [19]
Tsujita

[11] Patent Number: 5,879,284
[45] Date of Patent: Mar. 9, 1999

[54] ENDOSCOPE

[75] Inventor: Kazuhiro Tsujita, Kanagawa-ken, Japan

[73] Assignee: Fuji Photo Film Co., Ltd., Kanagawa-ken, Japan

[21] Appl. No.: 988,186

[22] Filed: Dec. 10, 1997

[30] Foreign Application Priority Data

Dec. 10, 1996 [JP] Japan .................................. 8-329549

[51] Int. Cl.⁶ ...................................................... A61B 1/04
[52] U.S. Cl. .............................................. 600/109; 348/71
[58] Field of Search .................................. 600/101, 109, 600/160; 348/70, 71

[56] References Cited

U.S. PATENT DOCUMENTS

| | | | |
|---|---|---|---|
| 4,882,623 | 11/1989 | Uchikubo | 348/71 |
| 4,885,634 | 12/1989 | Yabe | 600/109 |
| 4,891,696 | 1/1990 | Miyazaki | 348/71 |
| 4,961,110 | 10/1990 | Nakamura | 348/70 |
| 5,001,556 | 3/1991 | Nakamura et al. | 348/70 |
| 5,054,491 | 10/1991 | Saito et al. | 600/109 |
| 5,255,087 | 10/1993 | Nakamura et al. | 600/109 |
| 5,282,030 | 1/1994 | Nishimura et al. | 348/71 |
| 5,631,973 | 5/1997 | Green | 600/109 |
| 5,733,246 | 3/1998 | Forkey | 600/109 |

FOREIGN PATENT DOCUMENTS 711989  12/1995  Japan .

OTHER PUBLICATIONS

"Academy of Electronic Communication", Nov. 1984, vol. J67–D, No. 10 –No Translation.
"O plus E Magazine", Nov. 1986 –No Translation.
"Blind Deconvolution of Fluorescence Micrographs By Maximum–likelihood Estimation" by Vijaykumar Krishnamurthi, Yi–Hwa Liu, Santosh Bhattacharyya, James N. Turner and Timothy J. Holmes, Applied Optics magazine, vol. 34, No. 29, Oct. 10, 1995.

Primary Examiner—Paul J. Hirsch
Attorney, Agent, or Firm—Sughrue, Mion, Zinn, Macpeak & Seas, PLLC

[57] ABSTRACT

An endoscope includes an objective optical system which is inserted into a body and an image taking device which takes an image formed by the objective optical system and outputs an image signal representing the image. An image restoration processing is carried out on a part of the image signal corresponding to a predetermined range in the image taking range of the image taking device.

18 Claims, 4 Drawing Sheets

ENDOSCOPE

BACKGROUND OF THE INVENTION

1. Field of the Invention

This invention relates to an endoscope used to examine the interior of a body cavity and the like, and more particularly to an endoscope in which blur of the image due to insufficient depth of focus of the objective optical system can be avoided.

2. Description of the Related Art

There has been in wide use an endoscope to observe the interior of a body cavity or to give treatment observing the interior of a body cavity. Currently an electronic endoscope comprising an illuminating light projecting system which projects illuminating light onto a part inside of a body through optical fibers or like, an objective optical system which is inserted into the interior of the body and forms an image of the part by the light reflected at the part of the body and an image taking means which takes the image formed by the objective optical system is major.

On the other hand, there have been made various investigations on photodynamic diagnosis. The photodynamic diagnosis is a technique in which a photosensitive material which has affinity to tumor and emits fluorescence when excited by light is first administered to the tumor, excitation light having a wavelength in the excitation wavelength range of the photosensitive material is projected onto the tissue, and then the intensity of the fluorescence is measured or the tumor is diagnosed on the basis of an image formed by the fluorescence.

A fluorescence endoscope for taking such a fluorescence image and displaying the image basically comprises an excitation light projecting system which projects excitation light onto a part inside the body in addition to said illuminating light projecting system, the objective optical system and the image taking means, and an image formed by fluorescence emitted from the part is taken by the image taking means.

In such a fluorescence endoscope, use of an objective optical system which is small in F-number and high in numerical aperture is generally required in order to efficiently detect fluorescence which is normally very weak. However when a high numerical aperture objective optical system is used, the depth of focus is reduced and blur is apt to be generated in a part of the fluorescence image taken.

As an objective optical system for an endoscope in which the depth of focus can be increased, there has been known one disclosed, for instance, in Japanese Patent Publication No. 7(1995)-119893. The objective optical system is provided with a variable diaphragm and when a part relatively close to the optical system is to be observed, the diaphragm is closed to increase the depth of focus.

However since fluorescence emitted from a part inside the body is very weak as described above, the method of increasing the depth of focus by closing the diaphragm is difficult to apply to the fluorescence endoscope.

Though problems are described above in conjunction with the fluorescence endoscope which takes an image by weak fluorescence, there is a problem, also in an endoscope which takes a normal image, that as the amount of light entering the taking means is increased, the depth of focus is reduced.

SUMMARY OF THE INVENTION

In view of the foregoing observations and description, the primary object of the present invention is to provide an endoscope in which the amount of light entering the taking means can be increased and at the same time blur of the image due to a short depth of focus can be avoided.

In accordance with a first aspect of the present invention, there is provided an endoscope comprising an objective optical system which is inserted into a body and an image taking means which takes an image formed by the objective optical system and outputs an image signal representing the image and is characterized by having an image processing means which carries out an image restoration processing on a part of the image signal corresponding to a predetermined range in the image taking range of the image taking means.

In accordance with a second aspect of the present invention, there is provided an endoscope comprising an objective optical system which is inserted into a body and an image taking means which takes an image formed by the objective optical system and outputs an image signal representing the image and is characterized by having a distance measuring means which detects the distance between each point on a part of the body within the image taking range of the image taking means and the objective optical system, and an image processing means which carries out an image restoration processing on a part of the image signal corresponding to the part of the body whose distance from the objective optical system is within a predetermined range.

As the image processing means, those which carry out an image restoration processing by use of a point spread function of the objective optical system can be suitably used. When the image restoration processing is carried out on a part of the image signal corresponding to the part of the body whose distance from the objective optical system is within a predetermined range, it is preferred that the point spread function at the detected distance be used as the point spread function of the objective optical system.

It is preferred that the image processing means be arranged to use different point spread functions for a plurality of substantially concentric areas having their center on the optical axis of the objective optical system.

Each of the endoscopes described above may be provided with an excitation light projecting system which projects excitation light onto a part inside the body with the image taking means arranged to be able to take an image formed by fluorescence emitted from the part. In this case, it is preferred that the image processing means carries out the image restoration processing by use of point spread function according to the wavelength of the fluorescence, e.g. the point spread function at the peak wavelength of the fluorescence.

Further it is preferred that the image processing means be arranged to carry out the image restoration processing on a part of the image signal corresponding to a part of the body which is on the far side of the range of focus as seen from the objective optical system.

It is preferred that the image processing means carries out the image restoration processing on the image signal which has been subjected to processing for reducing the number of the picture elements.

When a variable diaphragm for changing the effective numerical aperture of the objective optical system is provided, it is preferred that the image processing means carries out the image restoration processing only when the diaphragm is full opened.

It is preferred that the endoscope be provided with a selecting means for selecting whether the image restoration processing is to be carried out.

Further it is preferred that the endoscope be provided with an image display means which can simultaneously display both an image reproduced on the basis of an image signal which has been subjected to the image restoration processing and an image reproduced on the basis of an image signal which has not been subjected to the image restoration processing.

It has been known that blur of an image can be effectively removed by an image restoration processing using a point spread function or the like of the objective optical system as a degradation function. Degradation functions of images can be roughly divided into those which represent degradation by a point spread function which can be analytically determined and those which represent degradation by a point spread function which cannot be analytically determined. When the image is blurred due to insufficient depth of focus of the objective optical system of the endoscope, the degradation by the point spread function can be known by actually measuring the input and output of the objective optical system and accordingly a degradation function in the former group can be suitably used. In this case, the image can be restored by deconvolution.

For degradation by a point spread function which cannot be analytically determined, the point spread function is estimated on the basis of the degraded image itself and the image can be restored by blind deconvolution.

When the image is restored by the deconvolution or the blind deconvolution, a filtering processing is generally applied. At this time, when noise can be ignored, the image can be restored by applying a so-called reverse filter to the degraded image.

On the other hand, when noise cannot be ignored, the image can be restored by use of a least square filter (wiener filter) which minimizes the mean square error between the original image and the restored image, a limited reverse convolution filter, or the like.

Such an image restoration processing is described in detail, for instance, in papers of "Academy of Electronic Communication", November, 1984, Vol. J67-D, No.10, and "O plus E" magazine", an extra number, November, 1986. All the image restoration processings described there can be used in the present invention.

Which part of the image taking range (angle of view) will be out of focus can be known in advance according to the condition of use of the endoscope, e.g., for observing the inside of the bronchus or the colon. For example, when the endoscope is used in a tubular organ 1 such as the bronchus or the colon as shown in FIGS. 3A and 3B, since the angle of view of the objective optical system 2 is generally very wide, about 100°, a part far from the objective optical system 2 is located at the center of the image taking range and a part close to the objective optical system 2 is located in the periphery of the image taking range, and accordingly the central portion of the image is outside the range of focus.

In the endoscope in accordance with the first aspect of the present invention, the range on which the image restoration processing is to be carried out is properly determined on the basis of such recognition. That is, in the endoscope, the image restoration processing is carried out on a part of the image signal corresponding to a predetermined range in the image taking range of the image taking means. For example, in the cases shown in FIGS. 3A and 3B, by setting a circular area of a predetermined radius at the center of the image taking range as the range on which the image restoration processing is to be carried out as shown in FIGS. 4A and 4B, the image restoration processing can be carried out substantially only on the part of the image signal corresponding to the part outside the range of focus (the part on the far side of the range of focus from the objective optical system 2).

When blur of the image due to insufficient depth of focus of the objective optical system can be avoided in this manner, a high numerical aperture objective optical system can be employed and accordingly the amount of light entering the image taking means can be increased.

When there is a possibility that the objective optical system 2 can be obliquely located to the tubular organ 1 as shown in FIG. 3B, the part which is outside the range of focus is shifted toward the edge of the image taking range in a certain direction as compared with the case where the objective optical system 2 located straight to the tubular organ 1 as shown in FIG. 3A. Accordingly, in such a case, it is preferred that the range on which the image restoration processing is to be carried out be enlarged outward as shown in FIG. 4B.

In the endoscope in accordance with the second aspect of the present invention, the distance between each point on a part of the body within the image taking range of the image taking means and the objective optical system (which corresponds to the distance between each point on a part of the body within the image taking range of the image taking means and the image taking means) is detected. When the image processing means is arranged to carry out the image restoration processing on a part of the image signal corresponding to the part of the body whose distance from the objective optical system is within a predetermined range, blur of the image of the part of the body outside the range of focus of the objective optical system can be removed by properly setting the range of the distance.

By determining the range on which the image restoration processing is to be carried out in advance or on the basis of the distance from the objective optical system, the operation of the image restoration processing can be reduced and generation of new blur due to unnecessary image restoration processing on the part of the image in focus can be prevented.

DESCRIPTION OF THE PREFERRED EMBODIMENT

Figure 1:
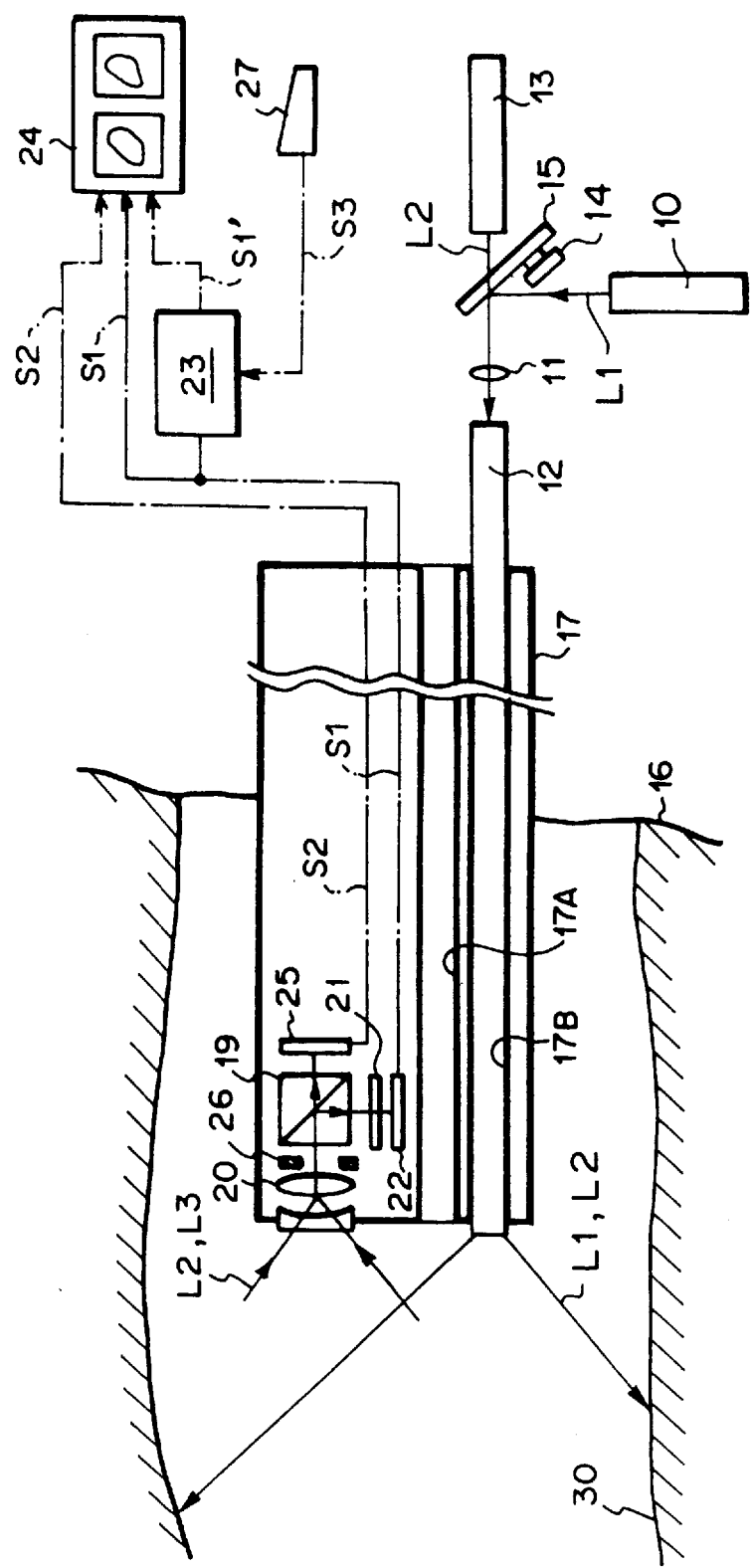
FIG. 1 is a schematic side view of a fluorescence endoscope in accordance with an embodiment of the present invention.

In FIG. 1, a fluorescence endoscope in accordance with an embodiment of the present invention comprises an excitation light source 10 which generates excitation light L1, for instance, in a blue region, a change-over mirror 15 which is moved into and away from the optical path of the excitation light L1 by a mirror drive means 14 and reflects the excitation light L1 at 90° when it is in the optical path of the excitation light L1, a condenser lens 11 which condenses the excitation light L1 and a light guide 12 which is formed of optical fibers and is disposed so that the condensed excitation light L1 enters the light guide 12. The endoscope is further provided with an illuminating light source 13 which emits white illuminating light L2 toward the condenser lens 11.

The light guide 12 is contained in a forceps passage 17B in a flexible probe 17 which is inserted into a body 16. A beam splitter 19 is disposed in the probe 17 and an objective lens 20 is disposed forward of the beam splitter 19.

The beam splitter 19 reflects downward a part of light impinging thereon and transmits the other part of the light as will be described later. A excitation light cut filter 21 and a fluorescence image taking means 22 are disposed in this order below the beam splitter 19. The fluorescence image taking means 22 may comprise, for instance, a CCD, and the fluorescence image taking means 22 is connected to an image processing system 23 and an image display system 24 which may comprise, for instance, a CRT. The light passing through the beam splitter 19 impinges upon a normal image taking means 25, which may comprise, for instance, a CCD. The normal image taking means 25 is also connected to the image display system 24.

Operation of the fluorescence endoscope will be described hereinbelow. A photosensitive material which has affinity to tumor and emits fluorescence when excited by light is first administered to a diagnostic part 30 of the body 16. The photosensitive material may be, for instance, porphyrin. When the excitation light L1 is projected onto the diagnostic part 30, the photosensitive material emits fluorescence and when the illuminating light L2 is projected onto the diagnostic part 30, the illuminating light L2 is reflected by the diagnostic part 30.

When a normal image is to be observed, the illuminating light source 13 is used, and the mirror 15 is retracted away from the optical path of the excitation light L1. The illuminating light L2 emitted from the illuminating light source 13 is condensed by the condenser lens 11 and enters the light guide 12. The illuminating light L2 propagates through the light guide 12 and emanates from the front end of the light guide 12 to illuminate the diagnostic part 30.

A part of the illuminated light L2 reflected by the diagnostic part 30 passes through the beam splitter 19 to impinge upon the normal image taking means 25. At this time, a normal image of the diagnostic part 30 by the reflected illuminating light L2 is formed on the normal image taking means 25 by the objective lens 20, and the normal image is taken by the normal image taking means 25. An image signal S2, representing the normal image, output from the normal image taking means 25 is input into the image display means 24 and the normal image is displayed by the image display means 24.

A variable diaphragm 26 is disposed between the objective lens 20 and the beam splitter 19 and is closed to a predetermined diameter to increase the depth of focus when the normal image is taken.

When a fluorescence image is to be taken, the excitation light source 10 is used and the mirror 15 is inserted into the optical path of the excitation light L1. The excitation light L1 emitted from the excitation light source 13 is condensed by the condenser lens 11 and enters the light guide 12. The excitation light L1 propagates through the light guide 12 and emanates from the front end of the light guide 12 to impinge upon the diagnostic part 30.

When the excitation light L1 is projected onto the diagnostic part 30, the photosensitive material which has been absorbed by the diagnostic part 30 emits fluorescence L3. A part of the fluorescence L3 is reflected by the beam splitter 19 to impinge upon the fluorescence image taking means 22. At this time a fluorescence image of the diagnostic part 30 by the fluorescence L3 is formed on the fluorescence image taking means 22 by the objective lens 20 and the fluorescence image is taken by the fluorescence image taking means 22. The excitation light L1 which is reflected by the diagnostic part 30 and travels toward the fluorescence image taking means 22 is cut by the excitation light cut filter 21.

An image signal S1, representing the fluorescence image, output from the fluorescence image taking means 22 is input into the image display means 24 and the fluorescence image is displayed by the image display means 24. Since the photosensitive material has affinity to tumor, only an image of the tumor part is basically displayed.

When the fluorescence image is taken, the variable diaphragm 26 is full opened so that the weak fluorescence L3 enters the fluorescence image taking means 22 as much as possible. When the variable diaphragm 26 is full opened, the depth of focus is reduced and blur is apt to be generated in a part of the fluorescence image taken. Removal of such blur will be described hereinbelow.

The fluorescence image signal S1 output from the fluorescence image taking means 22 is also input into the image processing system 23 and is subjected to an image restoration processing using a point spread function of the objective lens 20. Specifically a deconvolution processing using the aforesaid filters is carried out as the image restoration processing.

Out of such processings, a typical processing using a so-called reverse filter will be described below.

When a coordinate system for the whole image is expressed by (x, y) and a coordinate system for a part of the image is expressed by (x', y') while the original image and the degraded image are expressed respectively by f(x, y) and g(x, y), the following relation holds.

$$g(x, y) = \iint h(x, y, x', y') f(x', y') dx' dy' + n(x,y)$$

wherein, h(x, y, x', y') is a degradation function, and n(x,y) is noise. When there is no noise, a degraded image of a point light source represented by f(x', y')=δ(x'-α), y'-β) is h(x, y, α, β). Accordingly h(x, y, α, β) is a point spread function which is independent of the position (α, β) of a point on the original image.

A degraded image of a point does not exists in the position of the point except translation, the above relation is expressed by convolution as follows.

$$g(x, y) = \iint h(x-x', y-y') f(x', y') dx' dy' + n(x,y)$$

When it is assumed that noise is negligible, the above formula may be as follows.

$$g(x, y) = \iint h(x-x', y-y') f(x', y') dx' dy'$$

When taking Fourier transforms of the both sides of this formula and convolution theorem is applied thereto, the following formula holds.

$$G(u, v) = H(u, v) F(u, v)$$

wherein F(u, v), G(u, v) and H(u, v) are Fourier transforms of f(x, y), g(x, y) and h(x, y), respectively, and H(u, v) is a transfer function of a system for converting an original image f(x, y) to a degraded image g(x, y).

By taking a reverse Fourier transform of G(u, v)/H(u, v), the original image can be restored. Accordingly 1/H(u, v) is referred to as "a reverse filter".

Figure 4A:
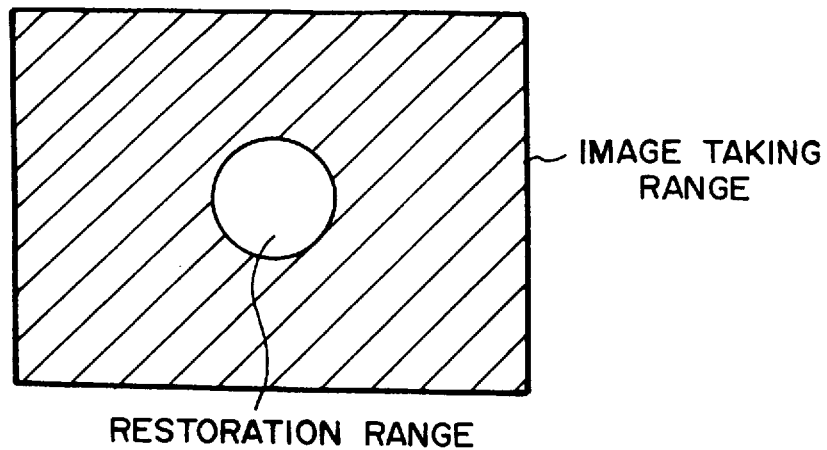
FIGS. 4A and 4B are views for illustrating the ranges on which the image restoration processing is to be carried out.
Figure 4B:
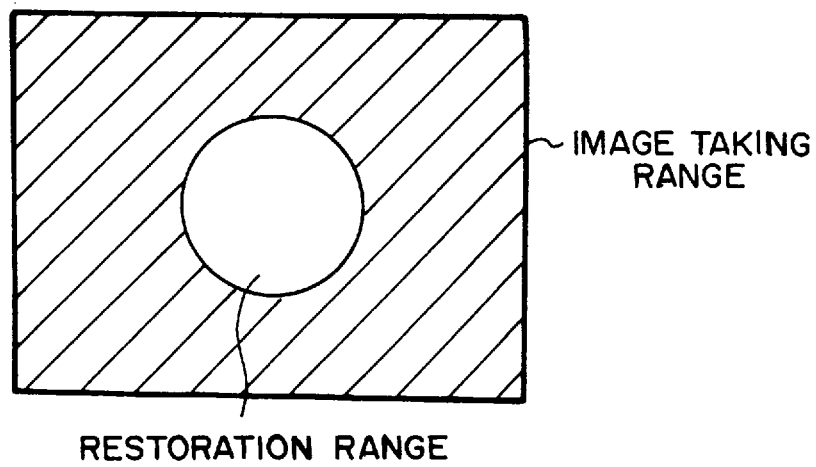

Since the diagnostic part 30 is a tubular organ such as the bronchus or the colon in this invention, the image restoration processing is carried out on the part of the image signal S1 corresponding to a circular area of a predetermined radius at the center of the image taking range as shown in FIG. 4A or 4B, whereby the image restoration processing can be carried out substantially only on the part of the image signal S1 corresponding to the part of the diagnostic part 30 outside the range of focus (the part on the far side of the range of focus) as described above in detail. This reduces the operation of the image restoration processing and facilitates real-time observation of the image, and at the same time prevents generation of new blur due to unnecessary image restoration processing on the part of the image in focus.

The image signal S1' which has been subjected to the image restoration processing is input into the image display means 24 and a fluorescence image is displayed by the image display means 24 on the basis of the image signal S1'. In this particular embodiment, the fluorescence image is displayed on the image display means 24 together with a fluorescence image reproduced on the basis of the original image signal S1.

This arrangement allows the restored image to be compared with the original image. When the effect of the image restoration processing is unsatisfactory, blur of the fluorescence image due to short depth of focus can be minimized by changing the point spread functions in sequence.

Though, in the embodiment described above, the range on which the image restoration processing is to be carried out is determined in advance, it is possible to provide a distance measuring means which detects the distance between each point on the diagnostic part 30 and the objective lens 20 and to carry out the image restoration processing on a part of the image signal corresponding to the part whose distance from the objective lens 20 is outside the range of focus of the objective lens 20.

As such a distance measuring means, for instance, an ultrasonic endoscope which is inserted into the body 16 through a forceps passage 17A in the probe 17 can be suitably employed. Though the ultrasonic endoscope is basically for obtaining information on the depth of the body from reflection of an ultrasonic wave, it can be used to detect the distance between each point on the diagnostic part 30 and the objective lens 20 since it can take reflection of a ultrasonic wave at the surface of an organ as a strong signal.

Further in the embodiment described above, the command for carrying out the image restoration processing on the image signal S1 is manually input by use of an input means 27 such as a keyboard. Accordingly, whether the image restoration processing is to be carried out can be selected.

However since blur is apt to be generated when the variable diaphragm 26 is in full open, it is possible to input the control signal of the variable diaphragm 26 also into the image processing system 23 and to automatically carry out the image restoration processing when the diaphragm 26 is full opened. This simplifies the operation of the operator.

Figure 2:
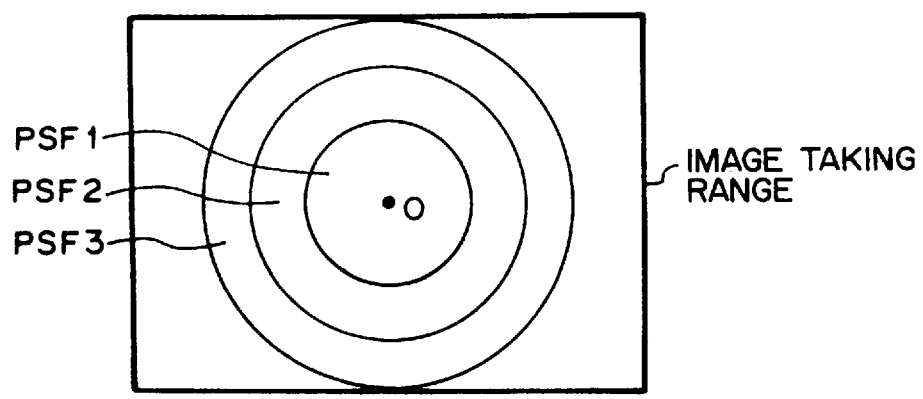
FIG. 2 is a view for illustrating an example of the relation between the point spread function and the image taking range.
Figure 3A:
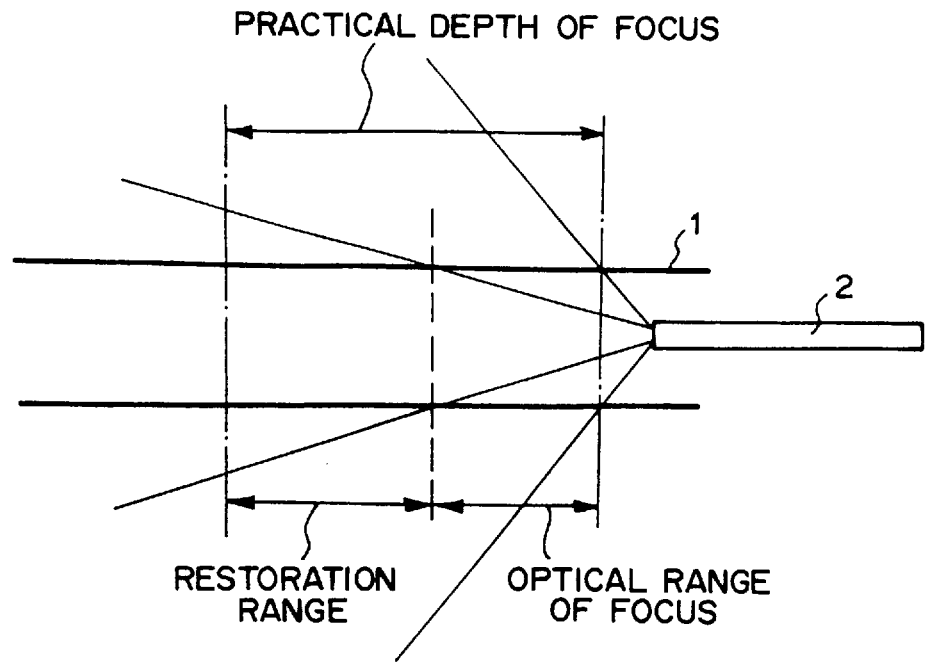
FIGS. 3A and 3B are views for illustrating examples of the relation between the objective optical system and the range in focus and the range on which the image restoration processing is to be carried out.
Figure 3B:
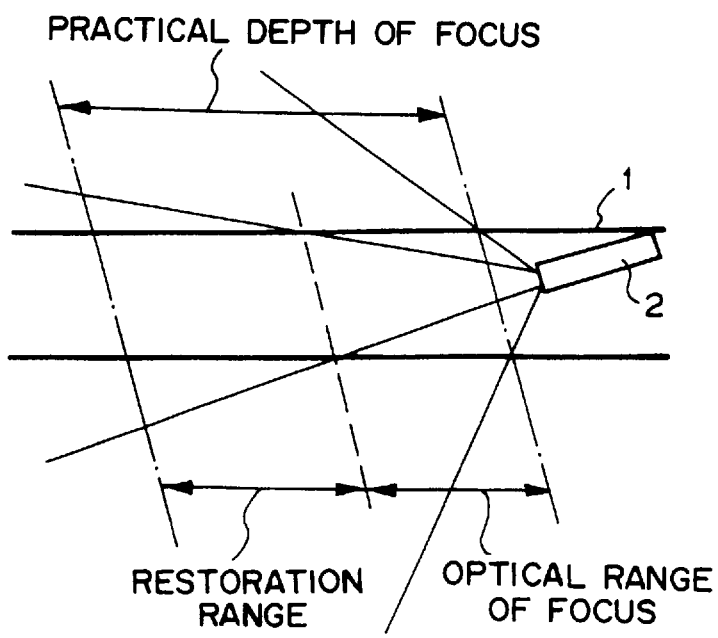

Instead of carrying out the image restoration processing by use of a single point spread function, it is possible to carry out the image restoration processing by use of different point spread functions for a plurality of substantially concentric areas having their center on the optical axis O of the objective optical system as indicated at PSF1, PSF2 and PSF3 in FIG. 2. This makes it feasible to carry out a better image restoration processing according to the degree of blur.

Further by use of a point spread function according to the wavelength of the fluorescence, a better image restoration processing can be carried out.

What is claimed is:

1. An endoscope comprising:

an objective optical system which is insertable into a body;

an image taking means having an image taking range which takes an image formed by the objective optical system and outputs an image signal representing the image, the image taking range including a restoration range and a residual range; and an image processing means which performs image restoration processing on a part of the image signal corresponding to the restoration range, but not on a part of the image signal corresponding to the residual range.

2. An endoscope as defined in claim 1 in which the image processing means carries out the image restoration processing by use of a point spread function of the objective optical system.

3. An endoscope as defined in claim 2 in which the image processing means uses different point spread functions for a plurality of substantially concentric areas having their center on the optical axis of the objective optical system.

4. An endoscope as defined in claim 2 in which an excitation light projecting system which projects excitation light onto a part inside the body with the image taking means arranged to be able to take an image formed by fluorescence emitted from the part, and the image processing means carries out the image restoration processing by use of a point spread function according to the wavelength of the fluorescence.

5. An endoscope as defined in claim 1 in which the image processing means carries out the image restoration processing on a part of the image signal corresponding to a part of the body which is on the far side of the range of focus as seen from the objective optical system.

6. An endoscope as defined in claim 1 in which the image processing means carries out the image restoration processing on the image signal which has been subjected to processing for reducing the number of the picture elements.

7. An endoscope as defined in claim 1 in which a variable diaphragm for changing the effective numerical aperture of the objective optical system is provided and the image processing means carries out the image restoration processing only when the diaphragm is fully opened.

8. An endoscope as defined in claim 1 further comprising a selecting means for selecting whether the image restoration processing is to be performed.

9. An endoscope as defined in claim 1 further comprising an image display means which can simultaneously display both an image reproduced on the basis of an image signal which has been subjected to the image restoration processing and an image reproduced on the basis of an image signal which has not been subjected to the image restoration processing.

10. An endoscope comprising:

an objective optical system which is insertable into a body;

an image taking means having an image taking range which takes an image formed by the objective optical system and outputs an image signal representing the image, the image taking range including a restoration range and a residual range;

a distance measuring means which detects the distance between (1) each point on a part of the body within the image taking range of the image taking means and (2) the objective optical system, the points on the part of the body which are greater than a predetermined distance from the objective optical system defining the restoration range of the image taking range; and an image processing means which performs image restoration processing on a part of the image signal corresponding to the restoration range, but not on a part of the image signal corresponding to the residual range.

11. An endoscope as defined in claim 10 in which the image processing means carries out the image restoration processing by use of a point spread function of the objective optical system.

12. An endoscope as defined in claim 11 in which the image processing means uses different point spread functions for a plurality of substantially concentric areas having their center on the optical axis of the objective optical system.

13. An endoscope as defined in claim 11 in which an excitation light projecting system which projects excitation light onto a part inside the body with the image taking means arranged to be able to take an image formed by fluorescence emitted from the part, and the image processing means carries out the image restoration processing by use of a point spread function according to the wavelength of the fluorescence.

14. An endoscope as defined in claim 10 in which the predetermined distance is greater than a range of focus of the objective optical system.

15. An endoscope as defined in claim 10 in which the image processing means carries out the image restoration processing on the image signal which has been subjected to processing for reducing the number of the picture elements.

16. An endoscope as defined in claim 10 in which a variable diaphragm for changing the effective numerical aperture of the objective optical system is provided and the image processing means carries out the image restoration processing only when the diaphragm is fully opened.

17. An endoscope as defined in claim 10 further comprising a selecting means for selecting whether the image restoration processing is to be performed.

18. An endoscope as defined in claim 10 further comprising an image display means which can simultaneously display both an image reproduced on the basis of an image signal which has been subjected to the image restoration processing and an image reproduced on the basis of an image signal which has not been subjected to the image restoration processing.

* * * * *